(12) United States Patent
Moavenian

(10) Patent No.: US 10,864,108 B2
(45) Date of Patent: Dec. 15, 2020

(54) FLANGE EXTENDER COMPRISING HONEY

(71) Applicant: Welland Medical Limited

(72) Inventor: Arash Moavenian, West Sussex (GB)

(73) Assignee: WELLAND MEDICAL LIMITED, West Sussex (GB)

( * ) Notice: Subject to any disclaimer, the term of this patent is extended or adjusted under 35 U.S.C. 154(b) by 504 days.

(21) Appl. No.: 15/113,388

(22) PCT Filed: Jan. 22, 2015

(86) PCT No.: PCT/EP2015/051288
§ 371 (c)(1),
(2) Date: Jul. 21, 2016

(87) PCT Pub. No.: WO2015/110552
PCT Pub. Date: Jul. 30, 2015

(65) Prior Publication Data
US 2017/0007440 A1 Jan. 12, 2017

(30) Foreign Application Priority Data
Jan. 22, 2014 (GB) .................................. 1401058.1

(51) Int. Cl.
A61F 5/449 (2006.01)
A61F 5/445 (2006.01)

(52) U.S. Cl.
CPC .............. A61F 5/449 (2013.01); A61F 5/445 (2013.01)

(58) Field of Classification Search
CPC combination set(s) only.
See application file for complete search history.

(56) References Cited

U.S. PATENT DOCUMENTS

| | | | | |
|---|---|---|---|---|
| 8,568,790 B2* | 10/2013 | Moloney | ............. | A61K 35/644 424/537 |
| 8,877,253 B2* | 11/2014 | Gammelsaeter | ....... | A61K 8/987 424/523 |
| 9,314,488 B2* | 4/2016 | Gammelsaeter | ....... | A61K 8/987 |
| 9,750,633 B1* | 9/2017 | Follenius | ................ | A61F 5/443 |
| 9,999,639 B2* | 6/2018 | Gammelsaeter | ....... | A61K 8/987 |
| 2003/0170308 A1* | 9/2003 | Cleary | ................ | A61K 8/0208 424/486 |
| 2004/0054313 A1* | 3/2004 | Molan | .................. | A61K 9/7007 602/42 |

(Continued)

FOREIGN PATENT DOCUMENTS

| DE | 102012104149 A1 | 11/2013 |
|---|---|---|
| GB | 2432120 A | 5/2007 |

(Continued)

Primary Examiner — Guy K Townsend
(74) Attorney, Agent, or Firm — Hathaway P. Russell; Erik A. Huestis; Foley Hoag LLP

(57) ABSTRACT

A flange extender for an ostomy bag comprises honey. In a preferred embodiment, the flange extender comprises a composition of hydrocolloid and medical grade Manuka honey and at least one release liner. Incorporation of honey into a flange extender provides additional adhesion to the skin of an ostomate and to a flange of an ostomy bag, increased wear time may possible and there may be reduced peristomal skin irritation. These advantages provide increased comfort for a user as well as reduced risk of infection through the antibacterial properties of honey.

10 Claims, 3 Drawing Sheets

(56) References Cited

U.S. PATENT DOCUMENTS

| | | | | |
|---|---|---|---|---|
| 2005/0287191 A1* | 12/2005 | Munro | | C08F 2/44 424/443 |
| 2006/0148352 A1* | 7/2006 | Munro | | A61L 15/60 442/118 |
| 2007/0282237 A1* | 12/2007 | Munro | | A61L 15/60 602/47 |
| 2009/0274770 A1* | 11/2009 | Gammelsaeter | | A61K 35/65 424/581 |
| 2009/0304780 A1* | 12/2009 | van den Berg | | A61P 17/02 424/447 |
| 2009/0311307 A1* | 12/2009 | Lykke | | B05D 3/00 424/443 |
| 2009/0317467 A1* | 12/2009 | Moloney | | A61L 26/0066 424/484 |
| 2010/0022961 A1* | 1/2010 | Dewey | | A61F 13/023 604/180 |
| 2011/0117071 A1* | 5/2011 | Barrett | | A61K 31/545 424/94.4 |
| 2011/0135726 A1* | 6/2011 | Munro | | A61L 15/60 424/484 |
| 2011/0238024 A1* | 9/2011 | Smith | | A61F 5/445 604/336 |
| 2015/0056295 A1* | 2/2015 | Gammelsaeter | | A61K 8/987 424/581 |
| 2015/0210951 A1* | 7/2015 | Aizenberg | | C10M 177/00 508/107 |
| 2015/0267042 A1* | 9/2015 | Munro | | C08L 33/26 524/28 |
| 2016/0120706 A1* | 5/2016 | Collinson | | A61F 13/0216 604/319 |
| 2016/0228475 A1* | 8/2016 | Gammelsaeter | | A61K 8/987 |
| 2016/0235582 A1* | 8/2016 | Moavenian | | A61F 5/443 |
| 2017/0007440 A1* | 1/2017 | Moavenian | | A61F 5/445 |
| 2018/0085408 A1* | 3/2018 | Moavenian | | A61L 26/0057 |
| 2018/0133360 A1* | 5/2018 | Bingol | | A61L 24/0089 |
| 2018/0303880 A1* | 10/2018 | Gammelsaeter | | A61K 8/987 |
| 2018/0338945 A1* | 11/2018 | Sambasivam | | A61P 31/04 |

FOREIGN PATENT DOCUMENTS

| | | |
|---|---|---|
| WO | 02087644 A1 | 11/2002 |
| WO | 2007/048193 A1 | 5/2007 |
| WO | 2007149958 A2 | 12/2007 |
| WO | 2012/134770 A1 | 10/2012 |

* cited by examiner

FLANGE EXTENDER COMPRISING HONEY

This application is the U.S. National Stage of International Patent Application No. PCT/EP2015/051288, filed Jan. 22, 2015, which claims the benefit of and priority to Great Britain Patent Application No. 1401058.1, filed Jan. 22, 2014, both of which are hereby incorporated by reference in their entirety.

The present invention relates to a flange extender comprising honey, which can be used to extend the flange of an ostomy bag, thereby increasing security of the connection between a user and the ostomy bag. The flange extender according to the present invention is especially suitable for medical purposes, in particular the flange extender can be used to maintain and promote healthy skin, in particular in the peri-stomal area.

BACKGROUND OF THE INVENTION

Ostomy bags are medical devices that are worn by an individual and they can be used for the collection of waste from a surgically diverted bowel or urinary system of the individual. They are used to collect waste that is output from a stoma created in the ostomate's skin and connected to the intestine or urinary system.

Known ostomy bags comprise a pouch or collection bag manufactured of film and in some cases the pouch is attached mechanically or with adhesive to a flange which forms a mounting plate, commonly referred to as a wafer or a baseplate. In use, the flange is fixed to the skin of an individual and the ostomy bag allows the waste to drain from a stoma into the pouch, while protecting the surrounding skin from contamination by the waste.

Ostomy bags should be air- and water-tight and they should allow the individual to lead an active normal lifestyle that can include all forms of sports and recreation. Generally there is a need to make ostomy bags discrete and secure.

The need to provide discrete ostomy bags must be balanced with the need to provide a sufficiently large collection bag so that unexpected deposits can be accommodated by the bag. In addition, the mounting plate must provide a secure attachment to the skin of an ostomate, but it must also be discrete and allow for the ostomy bag to be removed for emptying or disposal. Typically, ostomy bags are emptied at least once per day.

The need to change the device so frequently means a continued cycle of application and removal of the baseplate and flange extender. This can cause skin irritation, skin thinning, inflammation, redness, pain and make the compromised skin more susceptible to infection and further damage.

The flange which forms a mounting plate is commonly manufactured of a hydrocolloid and it is coated with an adhesive which serves to attach the ostomy bag to the skin.

Secure attachment of the ostomy bag to the skin is of great importance to the user and to the functioning of the product. The level of adhesion, however, varies from product to product and also from person to person, with different skin types and conditions. Loss of, or declines in, adhesion can have potentially difficult and embarrassing consequences for an ostomate, due to the nature of the waste in the pouch and unpredictable output of effluent from the stoma.

In addition to lack of adhesion in some cases, abdominal and peri-stomal irregularities pose another major concern; such irregularities, either as a result of herniation, surgery or anatomical deformity can further increase the risk of pouch detachment due to decreased adhesive contact area and difficulty in application. Thus, ostomates frequently feel that additional security is needed.

Flange extenders for ostomy bags are known. They attempt to address this issue. They are generally arc-shaped pads, typically manufactured of hydrocolloid, which are placed around the peripheral edge of the flange of an ostomy bag to provide an increased area for adhesion. The typical arc shape is based on the circular or near-circular flange shape itself, around which it is applied.

These known flange extenders, partly overlap the flange and provide additional adhesive support in the area immediately around the flange periphery. This goes some way to address the problem of a secure attachment, but does not address the issues around the continual application and removal of the appliance and the aforementioned consequences of compromised skin.

Flange extenders while providing additional security are not traditionally designed to help promote healthy peri-stomal skin which is exposed to constant application and removal of stoma care devices.

The present invention seeks to provide a flange extender which addresses one or more of the problems presented by prior art arrangements. In particular, the present invention seeks to provide a flange extender which may help to maintain or improve peri-stomal skin condition.

SUMMARY OF THE INVENTION

Remarkably, it has now been found that a flange extender comprising honey can be provided that provides a secure attachment, but which is discrete and does not compromise on comfort for the user. In this regard, the composition of the flange extender has therapeutic properties and helps to promote healthy skin around a stoma.

In accordance with the present invention, there is provided a flange extender for an ostomy bag wherein the flange extender comprises honey.

Preferably, the honey is medical grade honey. More preferably, the honey is medical grade Manuka honey.

Preferably, the flange extender comprises about 0.01% to about 2.0% honey by weight. More preferably, the flange extender comprises about 0.1-1.0% honey by weight.

Preferably, the flange extender comprises hydrocolloid. Preferably, the flange extender comprises about 95.0% to about 99.99% hydrocolloid by weight.

Advantageously, it has been found that the incorporation of honey into a flange extender provides additional adhesion to the skin of an ostomate and to a flange of an ostomy bag, increased wear time is possible and there is reduced peristomal skin irritation. These advantages provide increased comfort for a user.

Preferably, the flange extender can be produced in a multitude of geometries and dimensions to meet the needs for its intended application within ostomy and may also be tailored to a particular pouch or flange style.

The flange extender further comprises an adhesive coating. Preferably, the adhesive is acrylic based or silicone-based or PU-based. More preferably, the adhesive is acrylic based. Preferably, the adhesive coating is applied to at least a body facing surface of the flange extender.

In an alternative embodiment, the composition of the flange extender itself provides an adhesive.

Preferably, a flange extender according to the invention comprises no other materials.

Preferably, the flange extender further comprises at least one easy-release liner. The easy-release liner covers the adhesive until the flange extender is ready for use. Just before use, the easy release liner can be peeled away to expose the adhesive. This provides the advantage of protecting the adhesive until it is ready for use.

Preferably, the easy release liner comprises a tab which does not adhere to the adhesive. This provides the advantage that the tab can be easily gripped and facilitates removal of the easy-release liner to expose the adhesive.

Preferably, adhesive is applied to the body facing surface of the flange extender. More preferably, adhesive is applied to both the body facing surface and an ostomy bag facing surface of the flange extender. Such an adhesive may take the form a patterned adhesive mesh or perforated adhesive sheet.

Preferably, at least one easy release liner covers the adhesive on the body facing surface of the polyurethane film or both the body facing surface and an ostomy bag facing surface of the flange extender until the flange extender is ready for use. Just before use, the easy release liner can be peeled away from the flange extender surface or both the body facing surface and an ostomy bag facing surface of the flange extender to expose the adhesive. This provides the advantage of protecting the adhesive until it is ready for use.

In a preferred embodiment, the flange extender comprises a composition of hydrocolloid and medical grade Manuka honey, and at least one release liner.

Preferably, the flange extender is incorporated within the flange design of an ostomy bag and is integral with the ostomy bag. In this embodiment, the flange extender is applied to the flange of an ostomy bag and in use, a user is simply required to apply the flange extender to the skin.

Alternatively, the flange extender may be provided separately for use with an ostomy bag. In this embodiment, in use, a user is required to apply the flange extender to the skin and the flange of an ostomy bag. This can be achieved by applying the flange extender to the skin of an ostomate first followed by attachment of the flange extender to the flange of an ostomy bag. Alternatively, the flange extender is attached to the flange of an ostomy bag followed by attachment of the flange extender to the skin of an ostomate.

Preferably, the flange extender of the invention has a width of about 20 mm to about 50 mm. More preferably, the flange extender of the invention has a width of about 25 mm to about 45 mm. Most preferably, the flange extender of the invention has a width of about 30 mm. This provides the advantage of an increased area for adhesion and this provides added security.

Preferably, a flange extender according to the invention is stacked and packaged in a package. This has the advantage of protecting the flange extender.

Preferably, the package is of a moulded or vacuum formed plastics material, in which the flange extender is provided. Preferably, the package contains one or more flange extenders. More preferably, the package contains two or three or more flange extenders according to the invention, for example, about 10, about 20 or about 30.

In another aspect, the invention provides a composition comprising hydrocolloid and honey in the manufacture of a flange extender for reducing skin irritation and/or inflammation.

In another aspect, the invention provides a method for the production of a flange extender according to the invention, wherein the method comprises manufacturing a hydrocolloid and honey composition, cutting the composition to size, and applying an easy release liner.

BRIEF DESCRIPTION OF THE DRAWINGS

The invention will now be described by way of example with reference to the accompanying drawings, in which.

DETAILED DESCRIPTION OF THE INVENTION

It will be appreciated that aspects, embodiments and preferred features of the invention have been described herein in a way that allows the specification to be written in a clear and concise way. However, it will be appreciated that the scope of the invention may include embodiments having combinations of all or some of the features described. Unless circumstances clearly dictate otherwise, aspects, embodiments and preferred features can be variously combined or separated in accordance with the invention. In a preferred embodiment, a device in accordance with the invention comprises all aspects of the invention.

The word "about" is taken to mean optionally plus or minus 20%, more preferably optionally plus or minus 10%, even more preferably optionally plus or minus 5%, even more preferably optionally plus or minus 2.5%, most preferably optionally plus or minus 1%.

Within the context of this specification the word "comprises" is taken to mean "includes, among other things". It is not intended to be construed as "consists of only".

Within the context of this specification, the word "substantially" means preferably at least 90%, more preferably 95%, even more preferably 98%, most preferably 99%.

Figure 1:
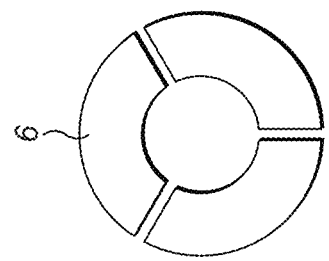
FIG. 1 shows a flange extender according to the invention. In the drawing the parts are identified by numbering as follows: (1): Flange, (2): Stoma hole, (3): pouch, (4): flange extender, (5): two-piece flange extender and (6): three piece flange extender.
Figure 1:
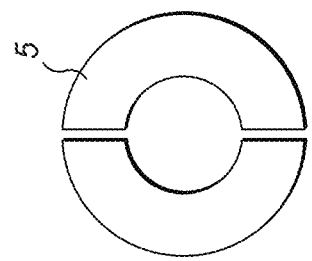
Figure 1:
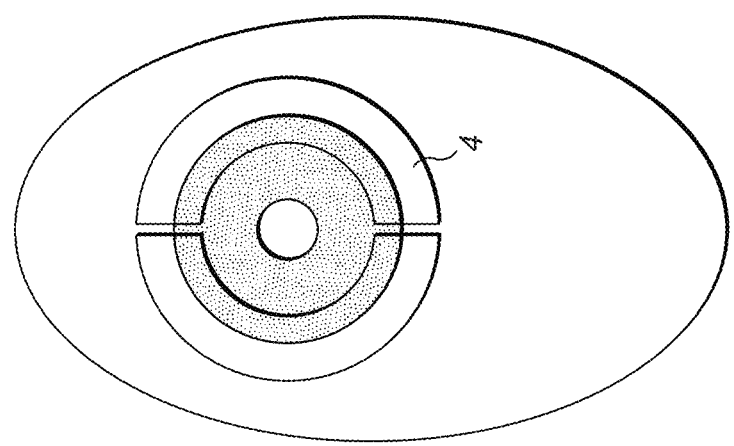
Figure 1:
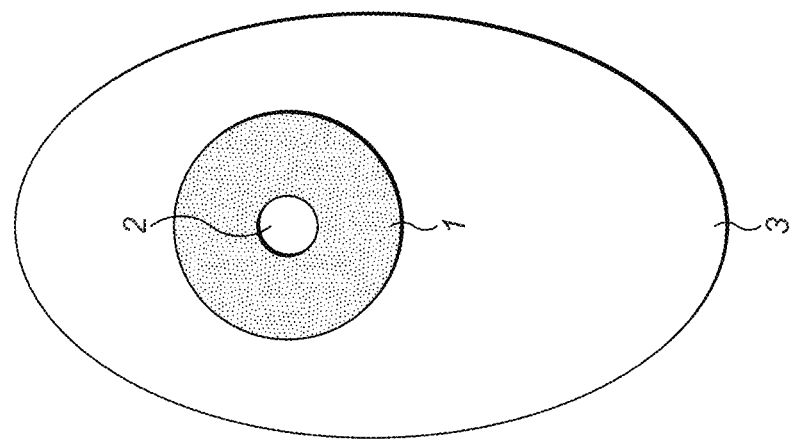
Figure 2:
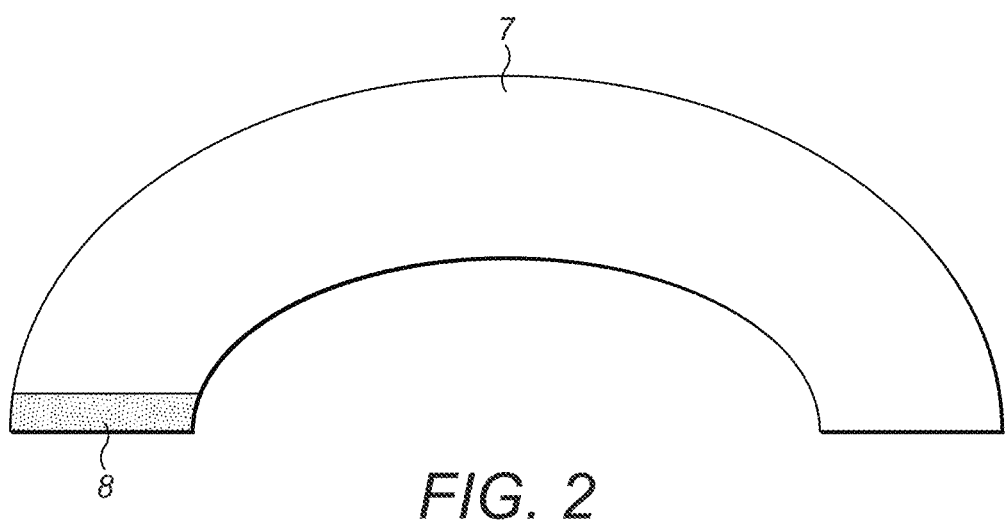
FIG. 2 a flange extender (4) according to the invention with non-adhesive area or tab (8), represented by shaded area.
Figure 3:
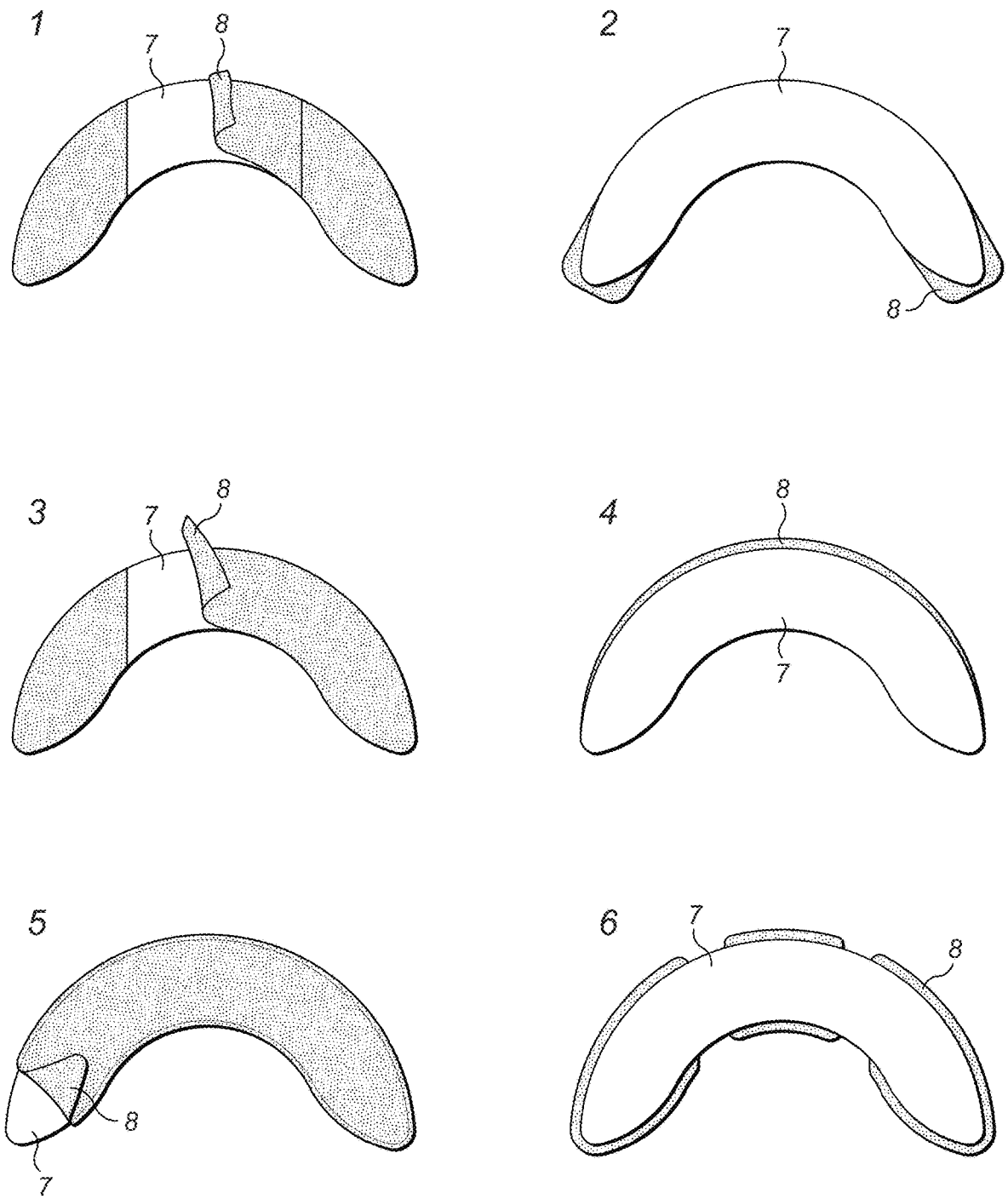
FIG. 3 shows schematics illustrating flange extenders (4) of the invention having one or more release liners (7).

Details of flange extenders according to the invention for use with ostomy bags are shown in FIGS. 1 to 3.

The ostomy bags have a flange (1), a stoma hole (2) and a pouch (3).

The flange extenders (4) (5) or (6) are manufactured of hydrocolloid and medical grade Manuka honey. They adhere to the skin of an ostomate and to the flange (1) of an ostomy bag.

A release liner covers the honey-hydrocolloid surface to be attached to the skin. The easy release liner (7) can be peeled away prior to use to expose the adhesive. This provides the advantage of protecting the adhesive until it is ready for use.

The easy release liner (7) comprises a tab (8) which does not adhere to the adhesive. This provides the advantage that the tab (8) can be easily gripped and facilitates removal of the easy-release liner (7) to expose the adhesive on the flange extender (4).

The flange extender (4) can be produced in a multitude of geometries and dimensions to meet the needs for its intended application within ostomy and may also be tailored to a particular pouch (4) or flange style (1). Examples of possible flange extenders (4) are shown in FIG. 3.

In one embodiment, the flange extender (4) (5) or (6) is incorporated within the flange (1) design of an ostomy bag and is integral with the ostomy bag. In this embodiment, the flange extender (4) (5) or (6) is applied to the flange (1) of an ostomy bag and in use, a user is simply required to apply the flange extender (4) (5) or (6) to the skin.

Alternatively, the flange extender (4) (5) or (6) may be provided separately for use with an ostomy bag. In this embodiment, in use, a user is required to apply the flange extender (4) (5) or (6) to the skin and the flange (1) of an ostomy bag. This can be achieved by applying the flange extender (4) (5) or (6) to the skin of an ostomate first followed by attachment of the flange extender (4) (5) or (6) to the flange (1) of an ostomy bag. Alternatively, the flange extender (4) (5) or (6) is attached to the flange (1) of an ostomy bag followed by attachment of the flange extender (4) (5) or (6) to the skin of an ostomate.

In one embodiment, the flange extender (4) (5) or (6) is sealed in a sachet prior to use. The sachet contains two or three flange extenders (4) (5) or (6).

To manufacture a flange extender (4) (5) or (6), a hydrocolloid and honey composition is provided and cut to size. The hydrocolloid and honey composition has an adhesive surface. An easy release liner (7), having a tab (8) for easy removal of the release liner (7) is applied to the adhesive surface.

The above described embodiments have been given by way of example only, and the skilled reader will naturally appreciate that many variations could be made thereto without departing from the scope of the claims.

The invention claimed is:

1. A flange extender for extending a surface area of a flange used with an ostomy bag having an opening, wherein:
   the flange extender comprises 0.01% to 2% honey by weight and 95% to 99.99% hydrocolloid by weight; and
   the flange extender is arcuate, having a concave inner edge, the concave inner edge adapted to attach to a peripheral edge of the flange;
   wherein at least two flange extenders have ends that are configured for: overlapping; and for alignment without overlapping; with each other, thereby forming an annulus when applied around the ostomy bag opening or to a peristomal area of skin of a user; and
   wherein the honey and the hydrocolloid are configured for reducing skin irritation and/or inflammation.

2. A flange extender according to claim 1, wherein the honey is medical grade Manuka honey.

3. A flange extender according to claim 1, wherein the flange extender is translucent or opaque.

4. A flange extender according to claim 1, wherein the flange extender comprises adhesive.

5. A flange extender according to claim 4, wherein the adhesive is provided by the composition of the flange extender or is acrylic based or silicone-based or PU-based.

6. A flange extender according to claim 4, wherein adhesive is applied to both the body facing surface and an ostomy bag facing surface of the flange extender.

7. A flange extender according to claim 4, wherein the flange extender further comprises at least one release liner.

8. A flange extender according to claim 7, wherein the release liner comprises a tab which does not adhere to the adhesive.

9. A flange extender according to claim 1, wherein the flange extender has a width of about 20 mm to about 50 mm.

10. A method of making a flange extender for extending a surface area of a flange used with an ostomy bag having an opening, the method comprising:
    providing a composition configured for reducing skin irritation and/or inflammation, the composition comprising 0.01% to 2% honey by weight and 95% to 99.99% hydrocolloid by weight; and
    providing a flange extender that is arcuate, having a concave inner edge, the concave inner edge adapted to attach to a peripheral edge of the flange; wherein at least two flange extenders have ends that are configured for: overlapping; and for alignment without overlapping; with each other, thereby forming an annulus when applied around the ostomy bag opening or to a peristomal area of skin of a user; and
    applying the composition to at least a skin-facing side of the flange extender.

\* \* \* \* \*